United States Patent [19]

Riordan

[11] Patent Number: Plant 6,126

[45] Date of Patent: Mar. 8, 1988

[54] ST. AUGUSTINEGRASS (PS-247)

[75] Inventor: Terrance P. Riordan, Lincoln, Nebr.

[73] Assignee: Pursley, Inc., Bradenton, Fla.

[21] Appl. No.: 828,328

[22] Filed: Feb. 4, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Harvey B. Jacobson

[57] ABSTRACT

A perennial St. Augustinegrass having rapid lateral spread, an outstanding root system, a dark green color, and good gray leafspot resistance. This variety has a good overall turf quality and performs well under sod production conditions.

2 Drawing Sheets

SUMMARY OF THE VARIETY

This invention relates to a new and distinct St. Augustinegrass. It was derived from a cross between a Texas Common selection (male parent) and a plant selected from open pollinated experimental 6-69-272 (female parent). This genotype first labeled 184 and later PS-247 was propagated vegetatively by stolons to provide planting stock for studying performance and making comparisons to commercially available cultivars.

Genotype PS-247 has a deep purple stigma color and a light purple anther color. It has a moderate leaf blade length and width, and internode length and width when compared to other cultivars. In field tests PS-247 had the longest stolon length, a rapid rate of cover, lowest gray leafspot (*Piricularia grisea*) incidence readings, and high turf quality ratings. In an aquaculture study PS-247 had a significantly greater number of roots and total root length than other St. Augustinegrass varieties in the test. This information can be used to distinguish PS-247 from other St. Augustine cultivars.

BRIEF DESCRIPTION OF THE ILLUSTRATIONS

FIG. 1 is a photograph of the leaves and stem of a PS-247 St. Augustinegrass plant, FIG. 2 shows a spike of a PS-247 St. Augustinegrass plant, FIG. 3 shows mowed turf of PS-247, and FIG. 4 shows the root development of PS-247 and other St. Augustinegrasses.

DETAILED DESCRIPTION OF THE VARIETY

Figure 1:
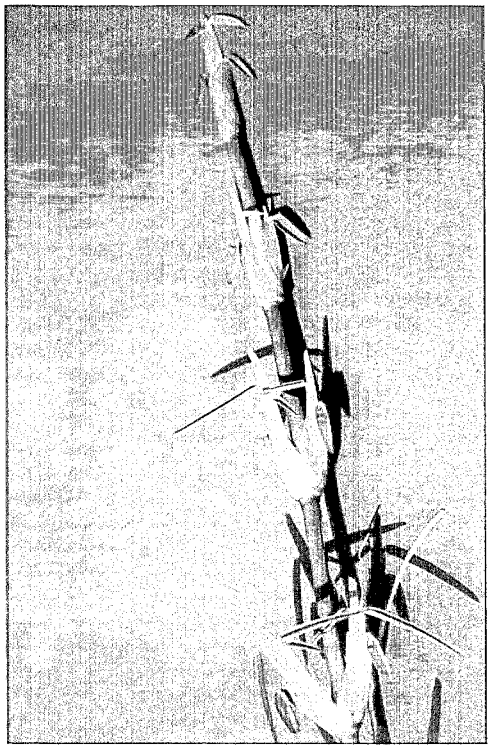
Figure 2:
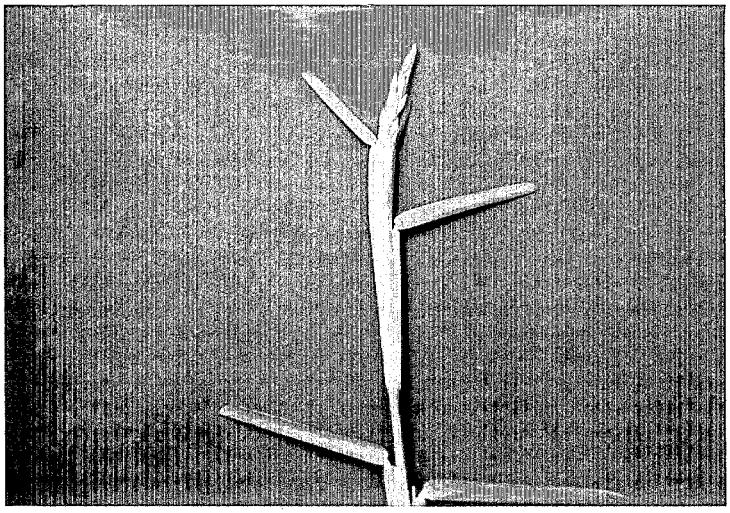
Figure 3:
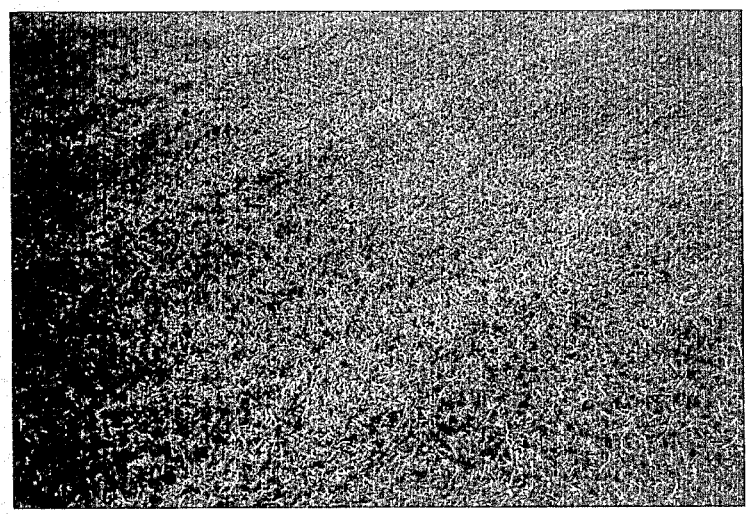
Figure 4:
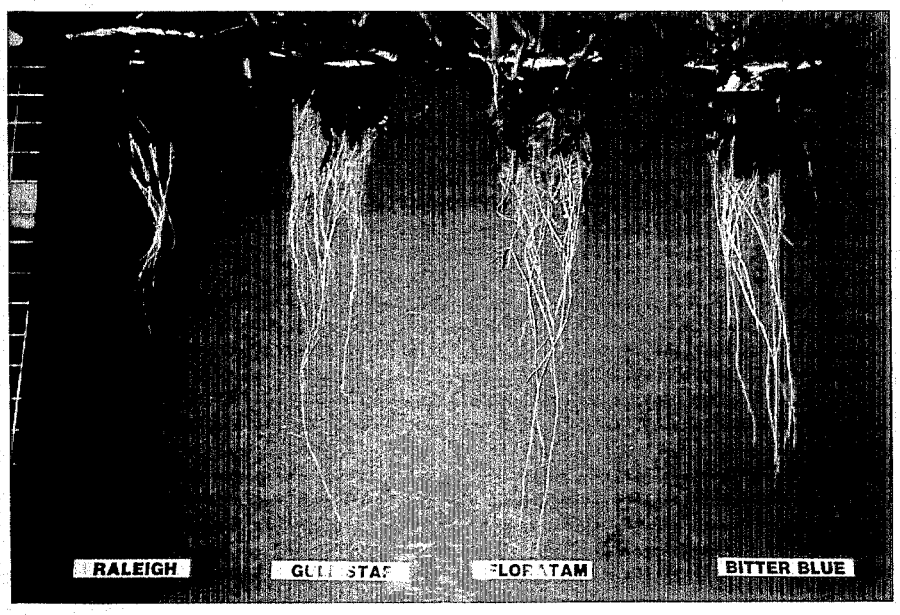

Genotype PS-247 possesses a Munsell color designation 5.0 GY 5/6[1/] and is characterized by compressed and branched culms. The leaf blades are moderate in length, averaging 34.6 mm and 49.0 mm for the first expanded leaf and the third leaf, respectively. The leaf blades are moderate in width, averaging 7.8 mm and 8.1 mm for the same leaves. The internode lengths and widths are also moderate in size, averaging 86.2 mm and 2.8 mm, respectively for the first expanded internode; and 97.4 mm and 2.7 mm, respectively for the third internode. This information and comparisons to commercially available cultivars, given in Tables 1 and 2, allow PS-247 to be distinguished from the semi-dwarf Seville and Floratam.

[1/] The Munsell designated color is of plant material grown in the greenhouse. The color is subject to variation depending upon the environmental conditions under which the grass is grown.

TABLE 1

| Selection-Variety | First Leaf Blade Length (mm)[2] | First Leaf Blade Width (mm)[3] | Third Leaf Blade Length(mm) | Third Leaf Blade Width(mm) |
|---|---|---|---|---|
| PS-247 | 34.6 ± 7.3 | 7.8 ± 0.5 | 49.0 ± 14.2 | 8.1 ± 2.2 |
| Tex. Com. | 31.2 ± 6.2 | 7.8 ± 0.6 | 33.8 ± 5.8 | 7.6 ± 1.0 |
| Seville | 22.0 ± 3.3 | 6.7 ± 0.5 | 30.0 ± 7.0 | 7.9 ± 0.7 |
| Raleigh | 38.0 ± 8.0 | 9.4 ± 1.1 | 49.9 ± 22.9 | 9.8 ± 1.4 |
| Floratam | 56.7 ± 13.6 | 9.6 ± 1.1 | 73.0 ± 25.0 | 10.1 ± 1.0 |
| Floratine | 34.7 ± 8.8 | 8.1 ± 0.8 | 23.7 ± 3.9 | 6.8 ± 1.0 |
| L.S.D.(.05) | 11.9 | 1.1 | 21.5 | 1.1 |

[2]All plant material grown unclipped in greenhouse.

[3]Measurements recorded 15 millimeters above leaf collar.

TABLE 2

| Selection-Variety | First Internode Length(mm) | First Internode Width (mm)[4] | Third Internode Length(mm) | Third Internode Width(mm) |
|---|---|---|---|---|
| PS-247 | 86.2 ± 22.6 | 2.8 ± 0.3 | 97.4 ± 21.6 | 2.7 ± 0.2 |
| Tex. Com. | 84.3 ± 16.3 | 3.1 ± 0.2 | 87.8 ± 19.0 | 2.9 ± 0.3 |
| Seville | 82.9 ± 17.9 | 2.6 ± 0.2 | 89.1 ± 10.0 | 2.6 ± 0.2 |
| Raleigh | 90.9 ± 15.2 | 2.9 ± 0.3 | 79.9 ± 21.1 | 2.9 ± 0.3 |
| Floratam | 104.4 ± 20.7 | 3.4 ± 0.5 | 134.5 ± 4.0 | 3.4 ± 2.1 |
| Floratine | 42.9 ± 34.3 | 2.9 ± 0.3 | 47.0 ± 25.8 | 4.3 ± 2.1 |
| L.S.D.(.05) | 27.7 | 0.4 | 25.0 | 0.8 |

[4]Internode width is recorded equidistant between the two nodes.

PS-247 has a more extensive root system than other St. Augustinegrasses when grown under aquaculture conditions. PS-247 had twice the number of roots and nearly twice the total root length of the other varieties. This information, given in table 3, can be used to distinguish PS-247 from other tested grasses.

TABLE 3

| Selection-Variety | Total[5] Root Lgth. (cm) | Total Root Number | Average Root Lgth. (cm) | Longest Root | Water Use(cm) |
|---|---|---|---|---|---|
| PS-247(A) | 551.3 ± 28.0 | 49.3 ± 1.7 | 11.2 ± 0.2 | 30.5 ± 2.9 | 5.8 ± 0.8 |
| PS-247(B) | 649.0 ± 85.3 | 57.3 ± 8.2 | 11.4 ± 0.8 | 30.8 ± 3.2 | 6.7 ± 0.3 |
| Seville | 201.7 ± 70.6 | 20.0 ± 6.7 | 10.0 ± 0.2 | 24.9 ± 6.7 | 5.3 ± 0.4 |
| Raleigh | 210.7 ± 14.6 | 23.7 ± 2.0 | 9.0 ± 1.1 | 22.5 ± 1.1 | 6.5 ± 1.4 |
| Floratam | 385.0 ± 55.7 | 27.7 ± 5.4 | 14.1 ± 1.2 | 41.1 ± 6.4 | 6.9 ± 0.4 |

TABLE 3-continued

| Selection-Variety | Total[5] Root Lgth. (cm) | Total Root Number | Average Root Lgth. (cm) | Longest Root | Water Use(cm) |
|---|---|---|---|---|---|
| Floratine | 320.3 ± 91.2 | 25.0 ± 8.2 | 11.4 ± 0.8 | 30.8 ± 3.2 | 6.7 ± 3.3 |
| L.S.D.(.05) | 108.3 | 8.6 | 2.7 | 9.4 | 1.5 |

[5]All root measurements and water use measurements made under aquaculture growth study in greenhouse.

The purple stigma color and the light purple anther color of PS-247 along with the unreduced chromosome number of 18 allow this genotype to be easily distinguished from other commercially available St. Augustinegrasses. PS-247 is the only St. Augustine which has this particular combination. This information and comparisons with other cultivars is given in Table 4.

TABLE 4

| Selection-Variety | Stigma Color | Anther Color | Chromosome Numbers[6] |
|---|---|---|---|
| PS-247 | Deep Purple | Light Purple | 18 |
| Tex. Com. | White | Light Yellow | 18 |
| Seville | Light Purple | Light Yellow | 18 |
| Raleigh | White | Med. Yellow | 18 |
| Floratam | Deep Purple | Deep Yellow | 27 |
| Floratine | Light Purple | Deep Yellow | 27 |

[6]Chromosome number determinations made on pollen mother cells.

An electroporesis study carried out by Dr. James O. Anderson of Vari-Ident Laboratories suggest that PS-247 could be distinguished from Texas Comman, Raleigh, and Seville using various standard enzyme stains on a protein extract.

The rapid rate of cover and the outstanding stolon length of PS-247 can be used to identify this variety when compared to the other St. Augustinegrasses. These characteristics are considered very important in a vegetatively propagated species marketed through sod. This information which shows the lateral aggressiveness of PS-247, Raleigh and Floratam is summarized in Table 5.

TABLE 5

| Selection-Variety | Rate of Cover 10/16[7] | 12/2 | 3/28 | Stolon Length(cm) 10/16 |
|---|---|---|---|---|
| PS-247 | 4.0 | 7.0 | 8.7 | 57.4 |
| Tex. Com. | 3.7 | 6.3 | 8.7 | 42.3 |
| Seville | 3.0 | 5.3 | 7.7 | 34.7 |
| Raleigh | 4.3 | 7.3 | 9.0 | 50.6 |
| Floratam | 3.7 | 7.3 | 8.7 | 43.8 |
| Floratine | 2.3 | 4.6 | 8.7 | 31.1 |

TABLE 5-continued

| Selection-Variety | Rate of Cover 10/16[7] | 12/2 | 3/28 | Stolon Length(cm) 10/16 |
|---|---|---|---|---|
| L.S.D.(.05) | 1.6 | 2.5 | 1.0 | 18.0 |

[7]Rate of Cover is rated with 1 = least cover and 9 = 100 percent cover.

Turfgrass quality and color, although not definitive in these early tests, indicate that PS-247 can be identified based on improved performance under test conditions. PS-247 was selected over 400 genotypes because of outstanding performance. Turfgrass quality and color ratings for 1984 and 1985 are given in Table 6.

TABLE 6

| Selection-Variety | Turfgrass Quality[8] 10/16 | 12/12 | 3/29 | Turfgrass Color[9] 10/16 | 12/12 | 3/28 |
|---|---|---|---|---|---|---|
| PS-247 | 6.3 | 6.0 | 6.3 | 7.0 | 7.3 | 7.0 |
| Tex. Com. | 6.7 | 6.0 | 6.3 | 6.7 | 7.0 | 6.0 |
| Seville | 6.3 | 4.7 | 6.0 | 7.0 | 6.7 | 7.0 |
| Raleigh | 6.3 | 5.7 | 6.7 | 6.7 | 7.3 | 7.7 |
| Floratam | 5.7 | 6.0 | 5.3 | 7.0 | 7.3 | 6.7 |
| Floratine | 5.7 | 4.7 | 4.3 | 6.7 | 6.7 | 6.3 |
| L.S.D.(.05) | 1.1 | 2.1 | 1.7 | 0.6 | 0.8 | 1.6 |

[8]Turfgrass Quality is rated with 1 = very poor quality and 9 = outstanding turfgrass quality.
[9]Turfgrass Color is rated as 1 = straw brown color and 9 = very dark green color.

PS-247 has shown strong levels of disease resistance in initial tests and observations. It has had low gray leafspot (*Pircularia grisea*) readings in bare soil establishment tests where innoculum sources are at their highest. This variety has not shown any downy mildew (*Sclerophthora macrospora*) in the greenhouse when surrounded by infected plants, and has been shown to be St. Augustine decline virus resistant in laboratory tests at Texas A & M. This information and comparisons to other plants are given in Table 7.

TABLE 7

| Selection-Variety | Gray Leafspot 10/16[10] | 12/12 | 3/28 | Downy Mildew 12/10 | S.A.D Virus[11] |
|---|---|---|---|---|---|
| PS-247 | 1.3 | 1.0 | 1.0 | 1.0 | R |
| Tex. Comm. | 1.3 | 1.0 | 1.0 | 1.0 | S |
| Seville | 3.0 | 1.7 | 2.7 | 4.0 | R |
| Raleigh | 1.7 | 1.0 | 1.0 | 1.0 | R |
| Floratam | 1.7 | 2.7 | 1.7 | 1.0 | R |
| Floratine | 2.3 | 1.3 | 1.7 | 1.0 | S |
| L.S.D.(.05) | 1.0 | 1.0 | 1.0 | — | — |

[10]Disease ratings are made with 1 = no infection to 9 = 100 percent infection.
[11]St. Augustine Decline Virus Resistance(R) and Susceptibility(S) were determined by Dr. Robert W. Toler, Texas A & M University.

I claim:

1. A St. Augustinegrass, substantially as herein described and illustrated, characterized by its rapid lateral spread and root length and numbers.

* * * * *